United States Patent
Jones

[11] Patent Number: 6,001,280
[45] Date of Patent: *Dec. 14, 1999

[54] OIL-SOLUBLE TRACER SOLUTIONS CONTAINING GADOLINIUM COMPOUNDS

[75] Inventor: Timothy G. J. Jones, Cottenham, United Kingdom

[73] Assignee: Schlumberger Technology Corporation, Ridgefield, Conn.

[*] Notice: This patent is subject to a terminal disclaimer.

[21] Appl. No.: 09/008,698

[22] Filed: Jan. 19, 1998

Related U.S. Application Data

[63] Continuation-in-part of application No. 08/564,000, Nov. 29, 1995, Pat. No. 5,711,900.

[51] Int. Cl.$^6$ .............. G01N 31/00; H01B 1/00; H01B 1/06; C09K 11/00; G01V 5/00
[52] U.S. Cl. .............. 252/408.1; 252/517; 252/518; 252/521.1; 252/645; 250/260; 507/905
[58] Field of Search .............. 252/408.1, 517, 252/578, 521, 521.1, 645; 250/260; 507/905

[56] References Cited

U.S. PATENT DOCUMENTS

| | | | |
|---|---|---|---|
| 3,784,828 | 1/1974 | Hayes | 250/106 L |
| 3,970,561 | 7/1976 | Sievers et al. | 210/198 |
| 4,166,215 | 8/1979 | Anderson . | |
| 4,166,216 | 8/1979 | Cubberly, Jr. . | |
| 4,233,508 | 11/1980 | Arnold . | |
| 4,423,152 | 12/1983 | Lewis et al. | 436/56 |
| 4,522,631 | 6/1985 | Mourao et al. | 44/57 |
| 4,755,469 | 7/1988 | Showalter et al. | 436/27 |
| 4,825,072 | 4/1989 | McWhirter et al. | 250/259 |
| 4,962,264 | 10/1990 | Forester | 585/648 |
| 5,047,632 | 9/1991 | Hunt | 250/302 |
| 5,108,636 | 4/1992 | Leising et al. | 252/62.54 |
| 5,306,911 | 4/1994 | Hunt | 250/302 |
| 5,407,560 | 4/1995 | Miyawaki et al. | 208/106 |
| 5,543,617 | 8/1996 | Roscoe et al. | 250/259 |
| 5,711,900 | 1/1998 | Jones | 252/408.1 |

*Primary Examiner*—D. Gabrielle Brouillette
*Assistant Examiner*—Monique T. Cole
*Attorney, Agent, or Firm*—Keith G. W. Smith; William B. Batzer

[57] ABSTRACT

A tracer solution suitable for use in measuring flow velocities in a borehole, includes: a) a gadolinium salt of a carboxylic acid of general formula

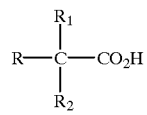

where R is an alkyl of not less than four carbon atoms, typically C4 or C5 alkyl, and $R_1$ and $R_2$ are hydrogen or an alkyl group, typically hydrogen, methyl or ethyl; b) a free branched-chain carboxylic acid such as an excess of the acid used to form the Gd salt; and c) a non-polar solvent such as hexane or heptane. The Gd content of the solution should be not less than about 50 g/l and is best when it is as high as possible, for example greater than 100 g/l, and the viscosity should be less than 20 cP.

10 Claims, No Drawings

OIL-SOLUBLE TRACER SOLUTIONS CONTAINING GADOLINIUM COMPOUNDS

This application is a continuation-in-part of prior application Ser. No. 08/564,000, filed on Nov. 29, 1995, now U.S. Pat. No. 5,711,900.

FIELD OF THE INVENTION

The present invention relates gadolinium-containing compounds for use in oil-soluble tracer solutions, and to tracers comprising such solutions. In particular the invention provides tracer compounds for use in a method of measuring the flow velocity of a hydrocarbon phase in a multiphase flow and finds application in measuring flow velocities in hydrocarbon-producing wells.

BACKGROUND OF THE INVENTION

The fluids produced by a hydrocarbon well typically comprise a hydrocarbon (oil) phase and an aqueous (water) phase and sometimes a gas phase. One of these phases, often the aqueous phase, is continuous and the other phase is dispersed therein. Knowledge of the proportions of these phases and their flow velocities is required to determine the flow rates from the well of the various phases. Many methods have been proposed for determining flow velocities in single-phase phase or multi-phase flows. One particular approach which is applicable to measuring flows in wells is to introduce tracers into the flow and to measure the passage of these tracers past a measurement station to make a measurement of the flow. One example of a tracer technique is the introduction of a saline solution into the flow and the measurement of the change in electrical conductivity as the tracer passes the measurement station. However, problems can arise due to the natural salinity of the formation water and such a technique only measures the aqueous phase and so cannot be used in isolation to provide all of the required measurements in a hydrocarbon well. As an alternative to saline solutions, radioactive tracers have been used to measure single-phase and multi-phase flows. These tracers can be made either oil-soluble or water-soluble and so the technique can be used to measure both phases in a hydrocarbon well. One example of the use of radioactive tracers to determine water flow behind casing (outside the well) is found in U.S. Pat. No. 3,784,828. An example of a tool used to make such measurements of flow inside hydrocarbon wells is the Tracer Ejection Tool of Schlumberger which is described in U.S. Pat. No. 4,166,215 and U.S. Pat. No. 4,166,216. Minor amounts of suitable radioactive tracer such as iodine 131 are periodically discharged into the continuous-phase well fluid at a selected depth location in the well. Thereafter, by simultaneously measuring the level of radioactivity above and below that location, measurements are obtained which are representative of one or more dynamic flow characteristics of the continuous phase. These measurements are based on the travel time of the tracer from the location where it is discharged into the flow to the measurement stations. Since the ejection of radioactive materials into the fluids that are subsequently produced from the well is often considered undesirable, alternative methods using nuclear radiation techniques have been proposed. These alternative techniques produce short-lived activation components in the flow to provide the radioactive material which is detected, but which is no longer radioactive by the time the fluids are produced from the well. An example of this is found in U.S. Pat. No. 4,233,508 in which the fluid being monitored is irradiated with neutrons such that oxygen atoms are transformed into radioactive nitrogen atoms which decay by emitting γ radiation which is detected at the measurement station. This method of activating a component of the flow only measures the aqueous phase since the oil phase does not include a significant concentration of oxygen atoms which become activated by neutron radiation. Further examples of the use of tracer ejection or activation techniques for measuring flows in wells are disclosed in U.S. Pat. No. 5,047,632 and U.S. Pat. No. 5,306,911.

U.S. Pat. No. 5,543,617 (incorporated herein by reference) discloses a method of measuring the flow velocity of one phase in a multi-phase flow, comprising the steps of creating a nuclear radiation environment around a measurement location in the flowing fluid at which radiation is detected; ejecting a tracer into the flowing fluid upstream of the measurement station which affects detection of the radiation at the measurement location as it passes; making a time-based measurement of the radiation at the measurement location to include passage of the tracer so as to determine the effect of the tracer on the detection of radiation; and using the time-based measurement to determine the flow velocity. A suitable tracer suggested for such a method is a gadolinium-containing compound. Suitable oil miscible tracers include gadolinium brine-in-oil emulsions and Gd tagged organic compounds which can also be oil-soluble. Brine-in-oil emulsions can be prepared using mineral oil, $GdCl_3$ brines, and a surfactant such as EMUL-HT. A suitable oil-soluble tracer has the general formula $Gd(RCOO)_3$ wherein R is typically $CH_3(CH_2)_4$. An alternative version of the tracer includes six additional $CH_2$ groups.

To be effective as a tracer in such a technique, it is necessary that the tracer include a relatively high concentration of gadolinium. It is known that high concentrations of transition metals such as lead, cobalt and manganese can be dissolved in non-polar organic solvents using naphthenic and related acids. The resulting compounds have been used in a variety of applications, including drying agents in paint, insecticidesibiocides and anti-knock additives in gasoline. A common feature of transition metal carboxylates is that their viscosities can be very high, even when dissolved in hydrocarbons at low concentrations; some heavy metal carboxylates have been used as lubricating greases. High viscosity is highly undesirable for a tracer for use in a technique such as that described in U.S. Pat. No. 5,543,617 since it prevents injection of controlled quantities into the flow and dispersion of the tracer throughout the oil phase prior to measurement.

THE ALKALINE-EARTH & HEAVY METAL SOAPS pp 66–69, S. B. Elliot (Reinhold Publishing Corp. NY, USA, 1946) proposes a number of compounds as "dispersion agents" or "flow agents" for use in modifying the viscosity of heavy metal soaps. These compounds have been found to modify the viscosity of the compounds and prolong shelf life. However, none of these applications involve elevated temperatures or conditions similar to those found in oil wells.

Oil-soluble lanthanide compounds have been proposed for various uses. U.S. Pat. No. 4,755,469 discloses the use, as an oil-soluble tracer, of a Group VIB, Group VIIB or lanthanum series rare earth salt of a fatty acid having 5–35 carbon atoms. It is proposed to add the tracer to an oil to be traced and oil samples taken at a remote location and analyzed to see if the tracer, and hence the original oil, is present at that location. The analysis techniques proposed are typical laboratory analyses and the metal in the tracer is chosen so as to be readily distinguished from common formation fluid components. U.S. Pat. No. 4,522,631 discloses a diesel fuel soluble compound of a rare earth metal (including Gd) for use as a fuel performance modifier. The compound typically has 3–25 carbon atoms and metal carbonyls are preferred. These compounds, together with an oxygenated compound such as an alkylcarbitol, aldehyde, ketone, alcohol or ether, are added to the fuel to provide a solution of 0.001–0.1 wt % rare earth in fuel.

None of the prior Gd compounds have been found suitable for use in a tracer flow velocity measurement technique.

It is an object of the present invention to provide a Gd compound in a form which is oil-soluble and has sufficient Gd content to be useful as a tracer in flow velocity measurement technique. Such a tracer ideally will have relatively low viscosity which is retained even though the tracer may be subjected to elevation of temperature or temperature cycling prior to use.

SUMMARY OF THE INVENTION

In accordance with a broad aspect of the invention, there is provided a low-viscosity, oil-miscible miscible, gadolinium solution, such as a tracer solution suitable for use in measuring flow velocities in a borehole, comprising: a) a gadolinium salt of a carboxylic acid of general formula

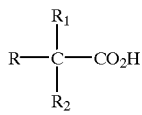

where R is an alkyl of not less than four carbon atoms, and $R_1$ and $R_2$ are selected from the group consisting of hydrogen and an alkyl group; b) a free branched-chain carboxylic acid; c) an oil-miscible solvent, especially an organic, non-polar solvent; and d) a viscosity stabiliser which maintains the viscosity of the solution at elevated temperatures.

It is particularly preferred that the solution has a viscosity of less than about 20 cP and a viscosity stabilizer such as tributyl citrate, oleyl alcohol, n-cyclohexyl-p-toluenesulfonamide and di(ethylene glycol) butyl ether can be included in the solution to maintain this level. It has been found that compounds such as these, which have been previously used as room temperature viscosity modifiers in other applications, can stabilise (rather than modify) the viscosity of a tracer solution containing Gd even when it encounters the elevated temperatures encountered in oil wells. Without the use of such a viscosity stabiliser, the viscosity of the solution will rapidly rise such that it becomes unusable as a tracer for fluid flow measurements.

The carboxylic acid forming the Gd salt preferably has R selected from C4 and C5 alkyl and $R_1$ and $R_2$ are selected from hydrogen, methyl and ethyl. When $R_1$ is hydrogen, $R_2$ is preferably methyl or ethyl. The Gd content of the solution should be not less than about 50 g/l and is best when it is as high as possible, for example greater than 100 g/l.

When the acid used to form the Gd salt is a branched chain acid, the free branched-chain carboxylic acid is typically the same as the acid used to form the Gd salt. When the acid forming the salt is not branched itself, i.e. $R_1$ and $R_2$ are hydrogen, a different acid must be present such as 3,5,5-trimethylhexanoic acid or 2-ethylhexanoic acid.

The non-polar solvent is typically a hydrocarbon having a density lower than that of water. Examples of suitable organic, non-polar solvents are hydrocarbons such as hexane and heptane. Suitable polar solvents might be long chain, branched alcohols, ethers or halogenated hydrocarbons.

The present invention is particularly preferred for use in the measurement of velocity of oil phases in the multiphase flows common in oil wells, and involves a technique which specifically chooses the capture cross section of thermal neutrons produced by moderation in the formation and the borehole of 14 MeV neutrons produced by a DT neutron generator as the tracer physical property which is probed. This technique is described in U.S. Pat. No. 5,543,617 (incorporated herein by reference). The detector used is preferably a scintillation detector which responds to capture γ rays. Other neutron generators and detectors are possible, e.g. spectroscopic γ ray detectors or γ count rate detectors; the above choices are convenient because they already exist in forms which can be placed in a borehole. As mentioned, the tracer has a capture cross section which is different from that of the flowing material, which can be a combination of water, oil and gas. Typical components of borehole oil, water and gas have capture cross sections of less than 10 barns, with the exception of chlorine, which has a capture cross section of 33 barns. Gd, which has a capture cross section of 49000 barns, in its isotopically natural form is therefore highly preferred for this method.

DESCRIPTION OF THE PREFERRED EMBODIMENT

The tracer solution according to the present invention finds particular application as a non-radioactive tracer for use in a method of measuring the flow velocity of an oil phase in the flow from a hydrocarbon well, particularly a horizontal well. In order to be useful in such a method, the solution should have as high a Gd content as possible in order to improve the detection of the tracer in the well. Since it is necessary to place the tracer in an oil phase and there is usually a water phase present, it is also desirable that the solution should have a density which is less than that of water and should be miscible or soluble readily in oil and have a relatively low viscosity.

The basic composition of a solution according to the invention comprises: a) a gadolinium salt of a carboxylic acid of general formula

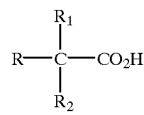

where R is an alkyl of not less than four carbon atoms, and $R_1$ and $R_2$ are selected from the group consisting of hydrogen and an alkyl group; b) a free branched-chain carboxylic acid; and c) a non-polar solvent.

The carboxylic acid forming the Gd salt preferably has R selected from C4 and C5 alkyl and $R_1$ and $R_2$ are selected from hydrogen, methyl and ethyl. Examples of suitable acids are hexanoic acid, 2-ethylhexanoic acid, neodecanoic acid, 2-methylhexanoic acid and 2,2-dimethylhexanoic acid.

The free branched-chain carboxylic acid is typically the same as the acid used to form the Gd salt. This can be achieved by use of an excess acid when producing the Gd salt as will be described below. The presence of free acid can also be found when an apparently stoichiometric quantity of branched chain acid is used in the production of the salt because it is not usually possible for the reaction to proceed to completion due to viscosity (i.e. it may not be possible to get a stoichiometric mixture to react to completion). When the acid forming the salt is not branched itself, such as hexanoic acid, a different acid must be present such as 3,5,5-trimethylhexanoic acid or 2-ethylhexanoic acid.

Examples of solutions according to the invention which have desired properties are summarized in Table 1 below:

TABLE 1

| Gd complex (Salt) | solvent | density (g/ml) | capillary viscosity[1] (cP) | Gd concentration (g/l) |
|---|---|---|---|---|
| 2-ethylhexanoate | heptane | 0.875 | 7.9 | 100.6 |
| 2-ethylhexanoate | hexane | 0.845 | 6.9 | 97.2 |
| 2-ethylhexanoate | heptane | 0.977 | 16.7 | 150.0 |
| 2-ethylhexanoate[2] | heptane | 0.837 | 19.8 | 100.0 |
| neodecanoate | heptane | 0.894 | 2.2 | 77.9 |
| 2-methylhexanoate | heptane | 0.840 | 2.2 | 100.0 |

[1] capillary viscosity measured at ambient temperature
[2] no excess acid added It is particularly preferred that the solution should maintain a viscosity of less than about 20 cP in use. Since temperature cycling and aging have been found to have a detrimental effect of some Gd complexes, a viscosity stabilizer such as tributyl citrate, oleyl alcohol, n-cyclohexyl-p-toluenesulfonamide and di(ethylene glycol) butyl ether can be used. These compounds in an amount of about 3% have been found to maintain viscosity in solutions according to the invention, tributyl citrate is particularly preferred in this respect. The compounds, including those indicated above, described in THE ALKALINE-EARTH & HEAVY METAL SOAPS pp 66–69, S. B. Elliot (Reinhold Publishing Corp. NY, USA, 1946) as "dispersion agents" or "flow agents" for use in modifying the viscosity of heavy metal soaps have been found to be suitable as viscosity stabilizers for the present invention. The applicability of these compounds is somewhat surprising since their normal activity is to modify the viscosity of the compounds at room temperature. In the present application, the stabiliser has no modifying effect on the viscosity of the Gd solution, a solution produced according to the methods described below will have the same viscosity as a solution produced without the use of a stabiliser. However, once this solution is heated, the absence of the stabiliser will mean that the viscosity will rapidly rise irreversibly and the solution becomes unusable. Since the increase in viscosity is thought to be due to an irreversible polymerisation reaction, any compound which inhibits this reaction without otherwise affecting the viscosity of the solution might be used.

Oleyl alcohol in an amount of 5% has been found to both stabilize viscosity and, when used in conjunction with tributyl citrate, break the formation of emulsions between the tracer solution and the brine phase of the flowing fluids in a well.

The synthesis of the gadolinium carboxylate tracers is, in principle, straightforward with a direct reaction between the carboxylic acid ($RCO_2H$) and hydrated gadolinium hydroxide ($Gd(OH)_3.xH_2O$):

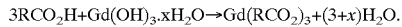

$$3RCO_2H + Gd(OH)_3.xH_2O \rightarrow Gd(RCO_2)_3 + (3+x)H_2O.$$

Gadolinium hydroxide is prepared by a precipitation reaction in water between a soluble gadolinium salt ($GdCl_3$, $Gd(NO_3)_3$, etc.) and a strong base:

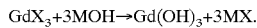

$$GdX_3 + 3MOH \rightarrow Gd(OH)_3 + 3MX.$$

The gadolinium hydroxide used in the reaction with carboxylic acids is rapidly precipitated, filtered and copiously washed with water followed by dry acetone. Washing the gadolinium hydroxide precipitate with acetone immediately after precipitation appears to suppress its crystallization and results in the amorphous hydroxide required to produce the complexes used in the present invention.

The preparation of gadolinium hydroxide can be optimised. Firstly, it has been found that the slow rate of filtration of the gelatinous precipitate of gadolinium hydroxide can be significantly improved by the addition of a high molecular weight water-soluble polymer such as polyacrylamide. Secondly, the reactivity of the dried gadolinium hydroxide powder is optimal if the washed precipitate is dried by vacuum desiccation rather than by heating. The optimal reactivity of the gadolinium hydroxide is obtained when the composition is approximately $Gd(OH)_3.5H_2O$. If the hydroxide is heated above about 60° C., then the composition is approximately $Gd(OH)_3.H_2O$ which is a less reactive form of the hydroxide and unreacted solid remains when the monohydrate is reacted with carboxylic acids. Sustained heating of amorphous gadolinium hydroxide will result in the undesired formation of crystalline gadolinium hydroxide.

The amorphous gadolinium hydroxide is reacted with the carboxylic acids at 85° C. (±5° C.) under constant mixing. The hydroxide is normally reacted with at least a 20% molar excess of a carboxylic acid. Examples of complexes have been produced using little or no excess acid, free acid is still found in the resulting complex. The high viscosity of the gadolinium carboxylate products prevents the reaction mixture from being stirred to completion.

Hydrated gadolinium carbonate ($Gd_2(CO_3)_3.xH_2O$) can be used in place of gadolinium hydroxide. However, since the carbonate has a lower metal concentration than the hydroxide, the increased solids content of the reaction mixture makes stirring more difficult and the reaction rate is considerably lower.

The gelled reaction mixture is allowed to cool to room temperature and hydrocarbon solvent (e.g., heptane) is added to give the required concentration of gadolinium, typically 100 g/l. The diluted reaction mixture is stirred to completion. The resulting product is a clear solution of low viscosity (<20 cP). Attempts to add the hydrocarbon solvent at elevated temperatures or prolonged heating of the solution to remove water (e.g., Dean-Stark distillation) can result in solutions of high viscosity, typically in excess of 200 cP. These high viscosities are not suitable for wellbore tracers because of difficulties with rapid injection into the flowing oil and subsequent mixing.

A tracer solution according to the invention can be made completely at ambient temperature by adding the dried amorphous gadolinium hydroxide (or carbonate) to the carboxylic acid(s) dissolved in the hydrocarbon solvent with the viscosity modifiers (e.g., tributyl citrate or oleyl alcohol). The acid is still added to an excess of about 20% by weight. The reaction proceeds cleanly and removes the need for heating the reaction mixture and, more significantly, the need to dissolve the gelled gadolinium carboxylate in the solvent which can be a slow and difficult process in large-scale manufacturing.

The filtration and drying of the gadolinium hydroxide precipitate to form a reactive solid is a slow and difficult process. In an attempt to circumvent these problems two additional methods have been developed to prepare the marker solution without the need to filter and dry the gadolinium hydroxide precipitate.

(i) The first method consists of reacting the freshly-precipitated gadolinium hydroxide slurry with the solution of carboxylic acid(s) and viscosity modifiers in the hydrocarbon solvent. A solution containing nominally 100 grams of gadolinium per litre of solution is prepared as follows. The gadolinium hydroxide is prepared by adding 237.5 g of gadolinium chloride hexahydrate in 281.2 g of deionised water to a solution containing 76.3 g of sodium hydroxide in 400 g of water. The slurried precipitate is stirred vigorously and 100 g of additional water added to the slurry and the slurry stirred for a further 30 minutes. The pH of the slurry is adjusted to be below a value of 7 by the addition of excess gadolinium chloride.

The marker solution is made by the addition of 330.2 g of 2-ethylhexanoic acid (20% excess) followed by 412.3 g of heptane and 32.9 g of tributyl citrate. The reaction is complete after about 3 hours to yield an initially cloudy solution which becomes clear after about 16 hours. The marker solution has a density of 0.884 g/ml and a metal content of 95.8 g/l and a capillary viscosity of 20 cP. The synthesis can be repeated using 40% excess 2-ethylhexanoic acid (385.2 g of acid, 370.7 g of heptane and 32.9 g of tributyl citrate) to give a marker solution with a density of 0.875 g/ml, a metal content of 97.9 g/l and a viscosity of 6.9 cP. The increased excess carboxylic acid content of the marker solution also results in rapid separation from the brine.

(ii) The second method of synthesising the marker solution is a further simplification which enables the separate stage of precipitating gadolinium hydroxide to be eliminated.

The second method consists of making an aqueous solution of sodium 2-ethylhexanoate by the addition of the sodium hydroxide solution (76.3 g in 400 ml of water) to the solution of 2-ethylhexanoic acid (385.2 g; 40% excess) and tributyl citrate (32.9 g) in heptane (370.7 g) followed by the addition of the gadolinium chloride solution. The reaction mixture is stirred vigorously during the addition of both the sodium hydroxide and the gadolinium chloride. The sodium 2-ethylhexanoate forms rapidly in the aqueous phase and the temperature of the reaction mixture reaches a maximum value of 56° C. The gadolinium 2-ethylhexanoate precipitated from the aqueous phase is readily solubilised by the heptane and the reaction appears to be complete after about 3 hours. The reaction mixture rapidly separates into a lower aqueous phase and an upper cloudy phase which clears over a period of about 16 hours; there is no residual unreacted solid. The marker solution has a density of 0.907 g/ml, a gadolinium content of 98.5 g/l and a capillary viscosity of 7.3 cP.

Several points should be noted about the two methods. Firstly, it is important that there is no sodium 2-ethylhexanoate remaining in the aqueous phase of the reaction mixture as it tends to stabilise emulsions between the marker solution and the brine phase. The presence of residual sodium 2-ethylhexanoate can be prevented by ensuring there is no excess sodium hydroxide present in the gadolinium hydroxide slurry prior to reaction with the carboxylic acid in the first method or by adding excess gadolinium chloride to the aqueous sodium 2-ethylhexanoate solution in the second method. Secondly, the viscosities of the gadolinium carboxylate solutions made by these two new methods are generally higher than those prepared from dried gadolinium hydroxide. The reason is that the water contents of the gadolinium carboxylate solutions are higher, presumably from content with a large volume of aqueous phase. The gadolinium carboxylate solutions are, however, perfectly usable as tracer solutions. The optimum solutions prepared by these two new methods usually have 40 weight percent excess acid and also contain 5 weight percent oleyl alcohol which acts both to reduce viscosity (in addition to the presence of tributyl citrate) and help to break the formation of any emulsion between the marker solution and the brine phase. Thirdly, the synthesis of tracer solutions of higher metal concentrations (typically 150 g/l) by these two alternative methods can lead to the problem of incorporation of water into marker solutions to form emulsions which can be stable for long periods of time, typically several months. The presence of emulsion phases are readily observed by their cloudy appearance. The emulsified water can be removed, and the organic solution clarified, by the addition of solid drying agents such as anhydrous calcium sulphate and potassium pyrophosphate, preferably with particle sizes in the range 0.5–2 mm. These drying agents can clarify the organic solutions over time periods of 1–2 days and can be readily removed from the solutions by filtering through a cotton wool filter.

In use, some formulations of Gd tracer solutions according to the invention can react with carbonate and bicarbonate ions in formation brines and precipitate gadolinium carbonate at the tracer-solution interface. This is undesirable since it can interfere with ejection of the tracer from a tool and prevent good mixing of the tracer with the oil phase. The addition of a second carboxylic acid to the solution, such as octanoic acid or 3,5,5-trimethylhexanoic acid, can inhibit the carbonate formation.

I claim:

1. A tracer solution comprising:
   a) a gadolinium salt of a carboxylic acid selected from the group consisting of hexanoic acid, 2-ethylhexanoic acid, neodecanoic acid, 2-methylhexanoic acid and 2,2-dimethylhexanoic acid;
   b) a free branched-chain carboxylic acid selected from the group consisting of 2-ethylhexanoic acid, neodecanoic acid, 2-methylhexanoic acid, 2,2-dimethylhexanoic acid and 3,5,5-trimethyl hexanoic acid; and
   c) a hydrocarbon solvent selected from hexane and heptane.

2. A tracer solution as claimed in claim 1, wherein the carboxylic acid forming the gadolinium salt is selected from the group consisting of 2-ethylhexanoic acid, neodecanoic acid, 2-methylhexanoic acid and 2,2-dimethylhexanoic acid, and the free branched-chain carboxylic acid comprises an excess of the selected acid.

3. A tracer solution as claimed in claim 1, wherein the carboxylic acid forming the gadolinium salt is hexanoic acid, and the free branched-chain carboxylic acid is selected from the group consisting of 2-ethylhexanoic acid and 3,5,5-trimethyl hexanoic acid.

4. A tracer solution as claimed in claim 1, further comprising octanoic acid as a carbonate inhibitor.

5. A tracer solution as claimed in claim 1, wherein the gadolinium salt comprises gadolinium 2-ethylhexanoate, the solvent comprises heptane and the tributyl citrate is present as a viscosity stabilizer in an amount of about 3%.

6. A low-viscosity, oil-miscible gadolinium solution, comprising:
   a) a gadolinium salt of a carboxylic acid of general formula

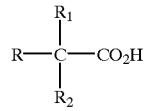

where R is an alkyl of not less than four carbon atoms, and $R_1$ and $R_2$ are selected from the group consisting of hydrogen and an alkyl group;
   b) a free branched-chain carboxylic acid; and
   c) an oil-miscible, organic solvent.

7. A tracer solution as claimed in claim 6 having a viscosity of less than about 20 cP.

8. A tracer solution as claimed in claim 6, wherein the gadolinium concentration is greater than about 50 g/l.

9. A tracer solution as claimed in claim 8, wherein the gadolinium concentration is greater than about 100 g/l.

10. A tracer solution as claimed in claim 1, wherein the carboxylic acid forming the gadolinium salt is selected from the group consisting of hexanoic acid, 2-ethylhexanoic acid, neodecanoic acid, 2-methylhexanoic acid and 2,2 dimethylhexanoic acid, and the free branched-chain carboxylic acid is selected from the group consisting of 2-ethylhexanoic acid, neodecanoic acid, 2-methylhexanoic acid and 2,2 dimethylhexanoic acid, the solution further comprising 3,5,5-trimethyl hexanoic acid as a carbonate inhibitor.

* * * * *